United States Patent [19]

Carbonari et al.

[11] Patent Number: 5,730,938
[45] Date of Patent: Mar. 24, 1998

[54] CHEMISTRY ANALYZER

[75] Inventors: Larry Alfred Carbonari; Jon D. Turpen, both of Toms River, N.J.

[73] Assignee: Bio-Chem Laboratory Systems, Inc., Lakewood, N.J.

[21] Appl. No.: 512,894

[22] Filed: Aug. 9, 1995

[51] Int. Cl.$^6$ .................................................. G01N 35/10
[52] U.S. Cl. ....................... 422/64; 422/63; 422/100; 436/43; 436/47; 436/49; 436/54; 436/164; 436/180; 73/864.22; 73/864.34; 134/21; 134/170; 134/171; 356/320
[58] Field of Search ........................... 422/63, 64, 67, 422/81, 100, 102; 436/43, 47, 48, 49, 50, 54, 174, 179, 180, 164; 73/864.22, 864.34; 134/170, 21, 171; 356/320

[56] References Cited

U.S. PATENT DOCUMENTS

| | | |
|---|---|---|
| 3,555,284 | 1/1971 | Anderson . |
| 3,690,772 | 9/1972 | Endl . |
| 3,690,833 | 9/1972 | Ferrari . |
| 3,748,911 | 7/1973 | Rousselet et al. ................ 73/423 |
| 3,836,329 | 9/1974 | Jordan ............................. 23/230 |
| 3,849,830 | 11/1974 | Wagner ............................ 15/302 |
| 3,880,589 | 4/1975 | Jones . |
| 4,053,284 | 10/1977 | Posch ............................... 23/259 |
| 4,200,607 | 4/1980 | Suzuki . |
| 4,227,886 | 10/1980 | Bullock et al. .................. 23/230 |
| 4,276,051 | 6/1981 | Ginsberg et al. . |
| 4,318,615 | 3/1982 | Sagusa et al. . |
| 4,318,885 | 3/1982 | Suzuki et al. ................... 422/68 |
| 4,319,830 | 3/1982 | Roach . |
| 4,324,556 | 4/1982 | Robertson et al. . |
| 4,338,280 | 7/1982 | Ambers et al. .................. 422/68 |
| 4,422,773 | 12/1983 | Cassaday et al. . |
| 4,499,053 | 2/1985 | Jones .............................. 422/68 |
| 4,516,437 | 5/1985 | Pedroso et al. ................. 73/864.22 |
| 4,528,158 | 7/1985 | Gilles et al. . |
| 4,537,510 | 8/1985 | Takahasi . |
| 4,549,809 | 10/1985 | Minekane et al. .............. 356/436 |
| 4,558,946 | 12/1985 | Galle et al. . |
| 4,559,664 | 12/1985 | Bohme et al. .................. 15/302 |
| 4,635,665 | 1/1987 | Namba et al. ................... 134/167 |
| 4,762,413 | 8/1988 | Namba et al. . |
| 4,817,443 | 4/1989 | Champseix et al. ............ 73/864.22 |
| 4,820,497 | 4/1989 | Howell . |
| 4,826,660 | 5/1989 | Smith . |
| 4,834,944 | 5/1989 | Wakatake ........................ 422/64 |
| 4,879,242 | 11/1989 | Tsukioka et al. . |
| 4,896,963 | 1/1990 | Kato ................................ 356/328 |
| 4,908,186 | 3/1990 | Sakamaki . |
| 4,913,179 | 4/1990 | Engel et al. ..................... 134/113 |

(List continued on next page.)

FOREIGN PATENT DOCUMENTS

| | | |
|---|---|---|
| 0 109 278 B1 | 1/1988 | European Pat. Off. . |
| 62-49259 | 3/1987 | Japan . |
| 62-242858 | 10/1987 | Japan . |

*Primary Examiner*—Long V. Le
*Attorney, Agent, or Firm*—William Squire

[57] ABSTRACT

A carousel receives a plurality of removable reagent containers, a turntable receives a plurality of sample fluid containers and a rotatable cuvette assembly holds an annular array of reaction and test cuvettes. A robotic arm carrying a fluid transfer needle coupled to a pair of syringes picks up one or more reagents and sample fluid for deposit into a cuvette. As the arm moves the needle tip exterior is washed and contaminants sent to a waste collector. At the end of a test cycle, the needle core is flushed and cleaned. A colorimetry photometric test is performed on the reacted fluids in each cuvette by a system employing ten interference filters, corresponding diode detectors and amplifiers employing two identical multiplexers providing identical filtered signals for logarithmic calculation of absorbance. The calculation subtracts a noise base level signal of one filter output from one multiplexer from a peak level signal produced by a second filter output from the other multiplexer for each component under test. A reciprocating plunger aspirates and cleans each cuvette at a single cleaning station employing multiple reciprocating motions. The photometric test is completed on all cuvettes in a single test cycle which are subsequently cleaned for the next test sequence.

22 Claims, 7 Drawing Sheets

U.S. PATENT DOCUMENTS

| | | |
|---|---|---|
| 4,929,847 | 5/1990 | Yamazoe et al. . |
| 4,942,017 | 7/1990 | Turpen . |
| 4,957,706 | 9/1990 | Romette et al. . |
| 5,051,238 | 9/1991 | Umetsu et al. ............................ 422/64 |
| 5,104,808 | 4/1992 | Laska et al. . |
| 5,147,610 | 9/1992 | Watanabe et al. . |
| 5,178,833 | 1/1993 | Covain ...................................... 422/64 |
| 5,192,505 | 3/1993 | Sakagami ................................. 422/64 |
| 5,250,440 | 10/1993 | Kelln et al. . |
| 5,270,007 | 12/1993 | Porte . |
| 5,270,210 | 12/1993 | Weyrauch et al. . |
| 5,270,211 | 12/1993 | Kelln et al. . |
| 5,271,899 | 12/1993 | Carbonari . |
| 5,289,385 | 2/1994 | Grandone . |
| 5,296,195 | 3/1994 | Pang et al. . |
| 5,298,428 | 3/1994 | O'Rourke et al. . |
| 5,312,757 | 5/1994 | Matsuyama et al. . |
| 5,314,825 | 5/1994 | Weyrauch et al. . |
| 5,318,359 | 6/1994 | Wakatake ................................. 366/140 |
| 5,358,691 | 10/1994 | Clark et al. . |
| 5,372,782 | 12/1994 | Karkantis et al. . |
| 5,387,979 | 2/1995 | Brauer et al. . |
| 5,408,891 | 4/1995 | Barber et al. ........................ 73/864.22 |

CHEMISTRY ANALYZER

This invention relates to an automatic chemistry analyzer, and more particularly, to a random analyzer for automatically conducting colorimetry photometric and other tests on body fluids such as blood, urine and so on.

The prior art includes a wide variety of automatic chemistry analyzers including random analyzers which involve the addition of a sample to a reaction vessel typically referred to as a cuvette, following which one or more reagents are added. The liquids are analyzed by fluorescent, radioactive or colorimetry photometric techniques.

For example, in U.S. Pat. No. 4,942,017, a chemistry analyzer is disclosed which employs a photometric analysis system including a rotary sample holder which periodically indexes to place a different cuvette in the optical path of a photometer employing colorimetric analysis. The photometric technique uses a light source which is chopped and applied to a dichroic filter. The filter light is applied through a cuvette holding the sample and reagent mixture to a photomultiplier tube. A number of control adjustments including individual potentiometers and gain adjustments were required on similar types of systems. A computer operates the system and displays the result on a printer or display. The filter comprises interference narrow bandwidth filters which produce various signals each manifesting the absorbance of different components in the sample under test. Tests are performed using well known procedures as known in the art. These type of photometers have a practical linear range of 0.0 to 2,000 absorbance units or 2.0 optical densities.

U.S. Pat. No. 5,271,899 discloses a particular type of chemistry analyzer for performing biochemical analysis. The disclosed process is for conducting enzyme-immunoassay (EIA) analysis. A measured amount of a sample which may contain a measured amount of a diluent is added to the reaction vessel. The vessel also holds a carrier having an antigen or antibody fixed thereto. One or more reagents may be then added. The test liquid is withdrawn from the reaction vessel and analyzed using a colorimetry photometer.

Other analyzers of more recent origin are known in which colorimetry photometry is performed directly in the cuvette or reaction vessel using a plurality of static narrow bandwidth filters of discrete wavelengths without using choppers as described above. In the latter technique, the light passed through the sample under test is focussed on a lens and separated into a plurality, for example, ten light signals. Each light signal is applied to a photodiode in an amplifier circuit including an operational amplifier with a parallel RC feedback network. A potentiometer is coupled to the amplifier for adjusting its gain. The gain is adjusted for setting the upper limit of the output signal.

The output signals of all of the amplifiers are applied to a combiner circuit whose output is applied to cascaded amplifiers employing further operational amplifiers. These signals are applied to a network including resistances including a further potentiometer for setting the lower limit of each of the combined signals which are applied to the resistor network serially. The lower limit potentiometer is set at a compromise value to set the lower limit of all of the test signals applied thereto.

The upper and lower limit settings for each filter calibrate a voltage output magnitude value for the corresponding signal. This calibration calibrates the absorbance values to correspond directly to a given voltage value for each component. This limits the effective range possible with the filtered output signals. When a signal exceeds this range, the sample is required to be diluted with a diluent and retested. These photometers have a practical linear range from 0.000 to 2,500 absorbance units or 2.25 optical densities. The voltage value between the preset upper and lower limits manifests the absorbance units value of each corresponding component of the sample under test. Since all ten different component filtered signals have their lower limit set by the same potentiometer this can produce variations in accuracy from component to component of the sample.

Also, drift and variations in gain and lower voltage limits as set by the factory for each instrument may have variations from instrument to instrument which variations are undesirable and which may be the source of further error in the final test results. The output absorbance voltage value is then converted to readings representing the value of the corresponding component present in the sample under test.

Other analyzers are shown in U.S. Pat. No. 4,762,413 to Namba et al., U.S. Pat. No. 5,314,825 to Weyrauch et al. and U.S. Pat. No. 4,558,946 to Galle disclosing automatic analyzing apparatus. All of the above patents are incorporated by reference herein.

A further problem concerns contamination of the transfer needle used to transfer reagents and samples to the cuvette. Each time the needle is immersed in the reagent or sample, the external surface of the immersed needle tip is wetted with the fluids and retains a residue of the fluids. The various fluids in the small diameter needle are each separated by an air bubble so they do not contaminate one another during transfer to the cuvette. Air bubble separation is effected by drawing a first liquid into the needle, followed by drawing air into the needle and then drawing a further liquid into the needle. These steps are controlled by control as known in the prior art.

Also, at the end of the transfer cycle for a given test the needle core also retains a residue of the prior transferred reagents and sample. The surface of the immersed needle tip needs to free of residual fluids prior to immersion in the next fluid to be picked up and transferred. Also, at the end of a test cycle, the needle core needs to be free of residual fluids to avoid contamination of the following reagents and sample to be tested. The prior art employs multiple operations for cleaning the needle, for example, returning the needle to a home station or a specially designated rinse container having a wash well into which the needle is immersed. These further operations are time consuming and slow the test procedure. By way of further example, reference is made to U.S. Pat. No. 5,271,899 which describes some of the prior cleaning procedures.

A further problem is directed toward cleaning the cuvettes. The cuvettes are attached fixed to a rotating wheel. After each test the cuvettes need to be cleaned for the next test. The cleaning involves aspiration of the test fluids in a first station, washing the cuvettes in a second station, aspirating the washing fluid and then drying the cuvette in a third station. These steps may also be repeated prior to commencing the next test. These cleaning steps are time consuming.

As a result, the prior art automatic chemistry analyzers have a throughput of about 75 tests per hour which adds to the cost of such tests. The present inventor recognizes a need for cleaning the needle and cuvettes during the test cycle without adding time to the test cycle time for cleaning purposes for increasing the throughput of a chemistry analyzer.

A chemical analyzer system according to the present invention comprises cuvette means including a plurality of cuvettes. Sample holding means hold a plurality of samples.

Reagent holding means hold at least one reagent. Transfer means include a needle having an external tip surface and a hollow core insertable into and for receiving at least a portion of one of the samples and at least a portion of the at least one reagent and for transferring the received portions to one of the cuvettes in a cycle. Needle washing means include means for washing the needle external surface during the transferring and for washing the needle core at the completion of the cycle.

In accordance with a further embodiment, cuvette washing means are included including means for reciprocating within the one cuvette subsequent to the testing for aspirating, washing and drying the one cuvette during the reciprocating.

IN THE DRAWING

FIG. 3a is a fragmented sectional side elevation view of a portion of the plunger used in the cuvette washing device in the embodiment of FIG. 3;

Figure 1:
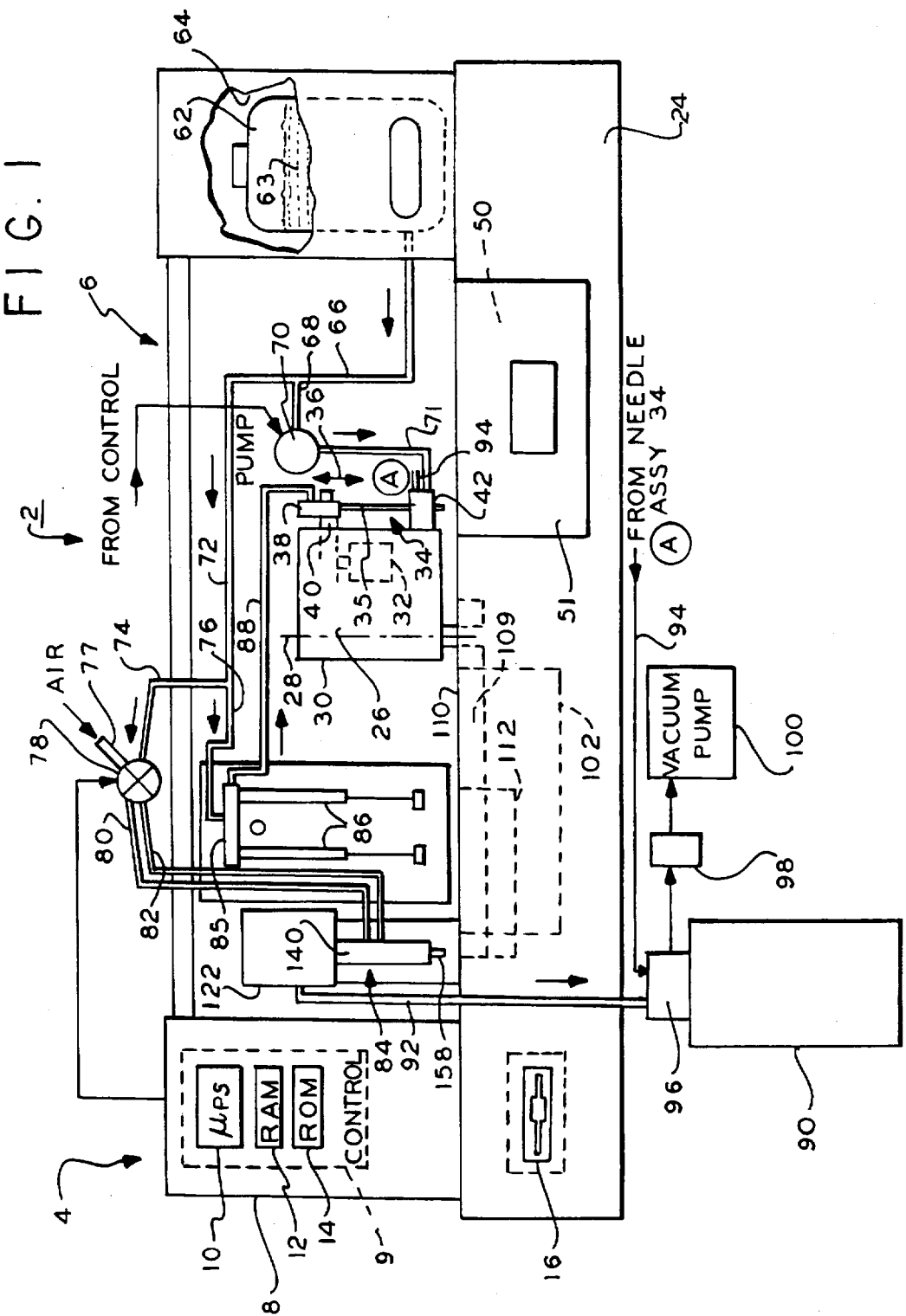
FIG. 1 is a diagrammatic side elevation view of a chemistry analyzer apparatus according to the present invention
Figure 2:
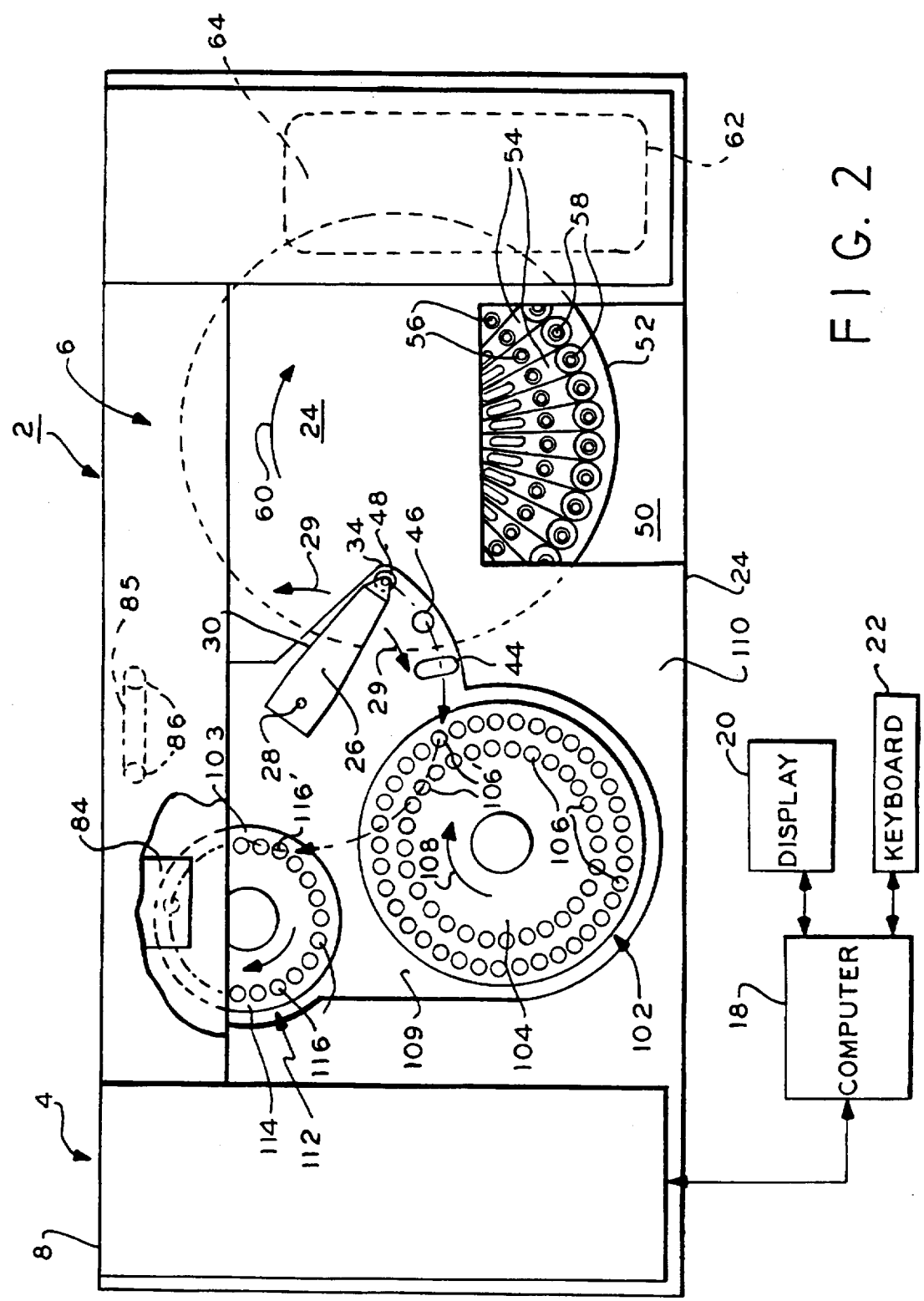
FIG. 2 is a diagrammatic plan view of the apparatus of FIG. 1.

In FIGS. 1 and 2, chemistry analyzer 2 for automatically conducting chemistry test on body fluids such as blood serum and urine and other fluids includes a control section 4 and a work station section 6. The control section 4 has a control 9 which is contained within and hidden within cabinet 8 and includes a plurality of microprocessors 10, for example, a 486 microprocessor manufactured by Intel Corporation and other microprocessors (not shown) such as Z80 type, RAM 12, ROM 14 and associated circuitry and components and power supply among others (not shown).

The microprocessors are programulated by a floppy disc containing the appropriate computer programs loaded into the system via floppy disc drive 16. As described in the aforementioned patents, and in the prior art generally, the specific components of the control section 9 and the control program can be implemented by one of ordinary skill in view of the description of the functions of the various components of the analyzer 2 described below.

In FIG. 2 the control section 4 is coupled to a computer 18, display 20, and a keyboard 22. The computer 18, display 20 and keyboard 22 preferably comprise an Apple Macintosh computer, model Power PC 7100AV, with 16 megabytes RAM memory and 500 megabytes hard disc memory and mouse. The computer 18 includes commercially available networking and export software for operation with the control section 4.

The computer 18 is used for interfacing with an operator for inputting patient data, selecting and setting up the tests including the fluids required to be performed and displaying the test results on CRT display 20 or a printer (not shown).

The display displays various menus for operating the system including a variety of tests and displays a variety of test related information such as, for example, displaying a menu of various tests to be selected, their results and a menu of the fluids required for selection by the operator, editing functions including test parameters, patient data, non-analyzer tests for peripheral test equipment connected to computer 18, reporting including printing reports, service and reminder functions.

The tests programmed to be performed are displayed on the CRT display 20, which displays the test status while in progress and the results of the tests. A further display includes a printer (not shown) for printing test results and other data. A built in quality control system monitors the tests for statistical deviations. All of these and other functions and parameters are within the skill of those of ordinary skill to implement.

The analyzer 2 is capable of fully automated in-vitro diagnostic processing of specimen test results. It can measure bi-chromatic readings of concentration (end-point) metabolite determinations, kinetic (rate) measurements of enzyme activity, fixed time substrate analysis, initial rate and linear or nonlinear Enzyme Immunoassay testing. The system has an open reagent system configuration which is capable of utilizing any commercially available liquid, reference chemistry reagent. Reagent test protocols such as selecting particular reagents and the sequence of application are programmable by the user via computer 18 and keyboard 22 and stored in memory. The test protocols are automatically adapted and implemented by the control 9. The system 2 is also a laboratory data management system for in-vitro diagnostic testing. The data management portion of the system 2 is provided by the computer 18, FIG. 2.

The computer 18 is programmable for panels of up to 500 tests per panel. It is programmed to receive and report data from several ancillary instruments such as hematology cell counters, urine strip readers and immunoassay chemistry analyzers. The computer 18 communicates with the analyzer 2 bi-directionally while the computer 18 communicates with the ancillary instrumentation simultaneously while the analyzer is performing chemistry testing. The work station 6 includes a number of different items and test features only some of which are shown. For example, an Ion Selective Electrode, ISE, module for Na, K, Cl and $CO_2$ electrolyte testing (not shown) is included. The items are carried by, or otherwise fixed to base 24 attached to cabinet 8 or attached to cabinet 8 as well.

A robotic modular arm 26 is rotatably secured to the base 24 for rotation about axis 28 in directions 29. The arm 26 comprises a hollow tapered housing 30 containing a stepping motor 32. A needle assembly 34 is attached to the arm 26 for displacement in directions 36 by motor 32 under the control of control 9. The needle assembly 34 includes a hollow tubular rigid metal member forming a needle 35, similar to a hypodermic needle but with a blunt end as will be described later and a diluent heater 38 secured to a support 40 driven in directions 36 by motor 32. A needle wash assembly 42 is fixed to housing 30 of the arm 26. The needle and wash assemblies are shown in more detail and will be described below in conjunction with FIG. 4. The arm 26 is rotated in directions 29 by a stepper motor (not shown) in the base 24 in response to control signals from control 9.

The base 24 includes a home member 44 which is thermoplastic. Member 44 is for normal quiescent reception of the needle 35. A pair of spaced apertures 46 and 48 spaced from member 44 are in the base in communication with a refrigerated compartment 50 recessed within the base 24. The compartment 50 houses a rotating reagent carousel 52.

The carousel 52 contains an annular array of radially extending reagent containers 54 sometimes referred to as boats. In this embodiment there may be 40 reagent containers 54 each having dual reagent compartments of respective 90 ml and 10 ml reagent capacity. The container 54 reagent compartments have access openings 56 and 58 which are selectively alignable to corresponding openings 46 and 48 in platform 110. Each compartment of a container 54 may hold a different reagent. The compartment 50 has a door 51 hinged to base 24 for accessing the carousel 52 for replacement of the reagent containers 54. The containers are each removably secured to and aligned by the carousel by control 9 to openings 46 and 48 in the order programmed by the user in any desired preprogrammed position in the annular array on the carousel 52.

A stepping motor (not shown) secured to the base rotates the carousel 52 in direction 60. The motor is operated by control 9 which positions the openings 56 and 58 of a given container aligned with respective apertures 48 and 46. Appropriate transmissions and connections are employed for connecting all of the stepping motors described herein to their particular driven component.

A diluent 63 storage container 62 is contained in a compartment 64 within cabinet 8 over the base 24. The container preferably has a capacity of 1.5 gallons. The diluent 63 is distilled water with chemicals added to form a diluent for the various fluids and to form a washing fluid source for the cleansing washer systems as described below. The diluent 63 is supplied to designated items throughout the system via flexible thermoplastic tubing such as tube 66. Tube 66 has a branch 68 which supplies diluent to pump 70 and a second branch 72, each branch being connected to tube 66 by a connector (not shown). The output of pump 70 is connected to washer assembly 42 via tube 71.

Pump 70 is driven by a stepper motor (not shown) via control 9 simultaneously with the operation of the arm 26. That is, every time arm 26 is in motion, the pump 70 is operating. When the arm is stationary, the pump 70 is off and not pumping.

The branch 72 is connected to two further branches 74 and 76 by a further connector (not shown). The branch 74 is connected to one input of a pinch valve 78. A tube 77 couples ambient air to a second input of the valve 78. Tube 80 selectively receives air supplied to the valve 78 from tube 77 and tube 82 receives diluent 63 supplied through the valve 78 from tube 74 depending upon the valve state.

Figure 3:
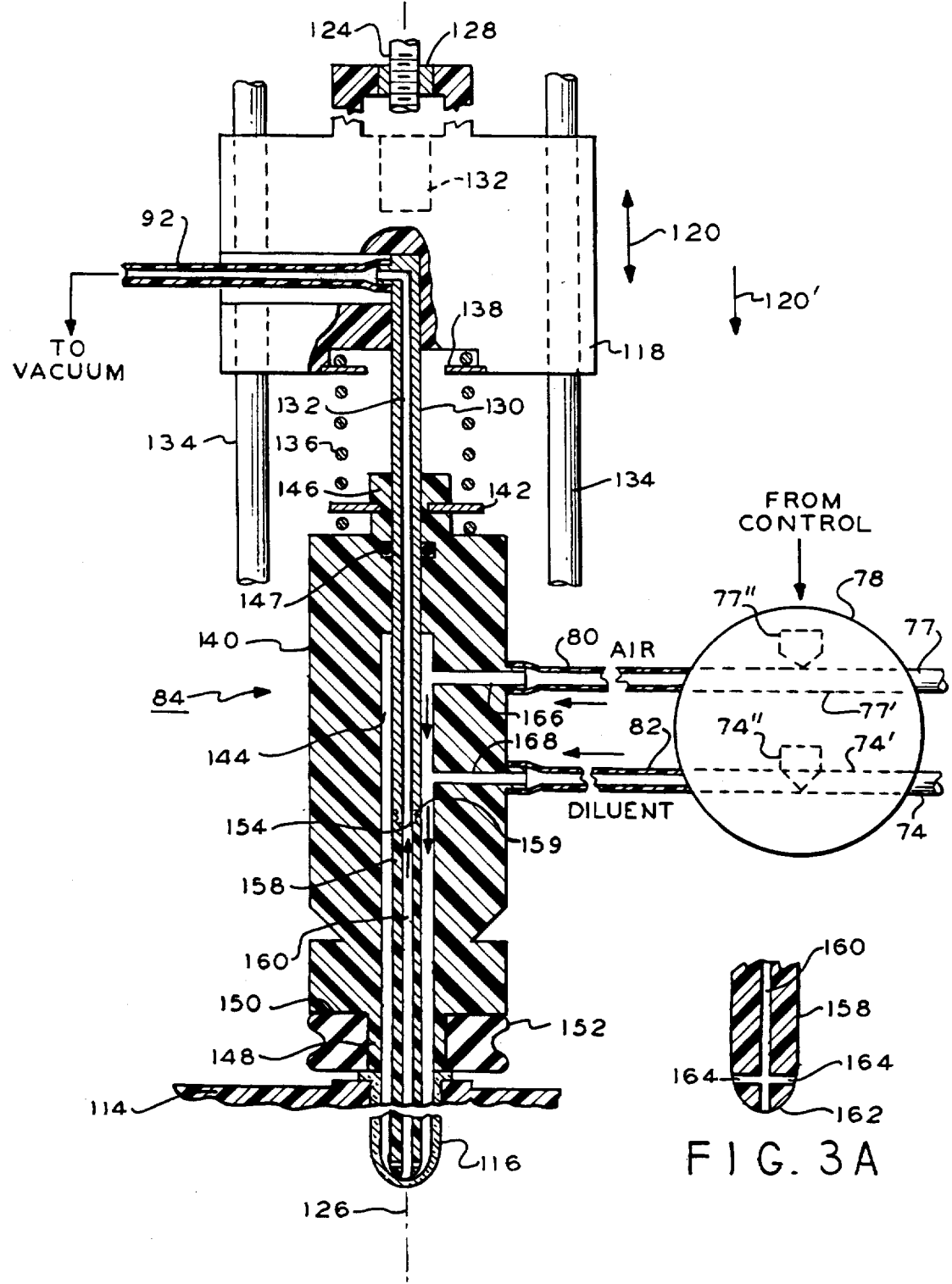
FIG. 3 is a fragmented sectional side elevation view of a cuvette washing device used in the embodiment of FIG. 1.

In FIG. 3, the valve 78 has dual passages 77' and 74' respectively coupled to the tubes 77 and 74 and tubes 80 and 82. The valve 78 includes pincers 77" and 74" to selectively connect either air from tube 77 to tube 80 or diluent from tube 74 to tube 82. Control 9 selectively operates the valve 78 to supply either air or diluent to tubes 80 and 82, respectively, one at a time. The tubes 80 and 82 are connected to cuvette washer assembly 84 attached to base 24 and cabinet 8.

The tube branch 76 is coupled to diverter/manifold 85 connected to syringes 86. A tube 88 couples the manifold 85 to heater 38 of needle assembly 34 to supply diluent 32 to the needle 35 through the heater 38. The syringes 86 and manifold 85 are operated to selectively pump measured amounts of diluent into or out of the needle 35 of needle assembly 34 in a known manner. That is, one syringe may be filling with a measured amount diluent fluid while the other may be pumping out diluent fluid to the needle. Also, the syringes 86 are used to pump all or measured amounts of fluid out of the needle 35. One of the syringes 86 preferably has a 500 microliter capacity for diluting the samples and the other syringe 86 has a 2500 microliter capacity for diluting the reagents. The control 9 operates the syringes to either fill the syringes with diluent for subsequent application to the needle 35 or to cause the needle 35 to withdraw fluids from the reagent or sample containers.

The diluent 32 pumped to the needle 35 serves to either dilute fluids contained in and previously picked up by the needle in preparation for a test or to flush out the needle 35 core at the end of a test cycle for cleaning purposes. The latter is to clean the core of contaminating fluids of a completed test in preparation for a new test cycle. The syringes are also used to empty measured amounts of fluid under test in the needles for use in a test and for picking up samples of fluid to be tested and reagents from the reagent containers 54. All of these operations are under the control of control 9 via stepping motors (not shown) which operate the syringes 86.

The system 2 further includes a waste collector 90, FIG. 1, which may be a 1.5 gallon container for collecting waste fluids. Output tube 92 from cuvette wash assembly 84 and output tube 94 from needle wash assembly 34 are connected as inputs to manifold 96. Manifold 96 separates waste liquid from air applied by tubes 92 and 94. The liquid is collected in collector 90 and the air is pumped through filter 98 by vacuum pump 100 to the ambient atmosphere.

System 2 further includes a sample carrier 102 comprising a turntable 104 to which fluid sample carrying containers 106 are releaseably secured. The containers 106 are preferably open ended tubes containing samples to be tested. The turntable 104 is mounted for rotation in direction 108 in a refrigerated recess 109 in platform 110 of the base 24. The carrier 102 is removable from the base 24. The containers 106 each contain a sample of body fluid to be tested such as blood serum or urine, for example. The carrier 102 has two concentric rows of containers 106 for holding preferably about 70 containers 106.

Each container in the turntable 104 is assigned a sequentially numbered location which is preassigned in the program of control 9. One of the locations is referenced as the number one or start position for the testing cycles. Each other container 106 position is numbered consecutively for purposes of programming the control 9 for sequential or randomly conducted tests. Appropriate patient and test parameters are entered into the system at the keyboard 22 by an operator for each position on the turntable 104 in use corresponding to the sample fluid filled containers 106. Not all sample positions need be in use during a given test run. The carrier 102 is rotated by a stepping motor (not shown) under control of control 9. The syringes cause needle 35 to pick up samples preferably having a volume in the range of 1 to 50 microliters.

Cuvette assembly 112 is mounted in the same recess 109 as sample carrier 102. In FIG. 2, the cuvette assembly 102 comprises a turntable 114, preferably molded thermoplastic, as is the turntable 104 of the sample carrier 102 and the carousel 52 for the reagent containers, all of which are unidirectional. The turntable 114 carries an annular array of cuvettes 116, preferably 25. The cuvettes are permanently fixed to the turntable 114. The turntable 114 is next to the sample carrier 102, smaller in diameter and is positioned so that the cuvettes each pass beneath the cuvette wash assembly 84. The cuvette assembly 112 is selectively rotated in direction 118 by a stepping motor (not shown) under the control of control 9.

The cuvettes of assembly 112, the sample holding containers 106 of carrier 102 and the reagent containers 54 of carousel 52 are all located so as to be rotated to predetermined positions for alignment with the needle 35 of needle assembly 34 as the needle assembly is rotated by arm 26 in directions 29. In particular, sample holding containers 106' and cuvette 116' are in a position that is aligned with the needle when the needle assembly 34 is at that position. Since FIGS. 1 and 2 are diagrammatic, the scale and exact positions of the various items may differ somewhat from that shown to effect the spaced relations described.

Each cuvette 116 is an optically clear circular cylindrical tube open at its upper end (FIG. 5) for receiving needle 35 and the mechanism from wash assembly 84. In FIG. 3, the cuvette wash assembly 84 comprises a thermoplastic molded support 118. A stepping motor (not shown) responsive to control 9 is mounted in housing 122 (FIG. 1) secured to cabinet 8. The motor rotates feed screw 124 about axis 126. The feed screw 124 is threaded to threaded insert 128 secured to support 118. As the screw 124 rotates, the support 118 is displaced vertically in directions 120. The screw 124 may also pass into bore 132 in the support 118 as the support is displaced.

As the screw rotates, the shaft 130 remains stationary and is lifted or lowered in directions 120 with the support 118. The hollow core 132 of shaft 130 is coupled to tube 92. The support 118 is guided vertically by guide rods 134 secured to the cabinet 8 and base 24.

A coil compression spring 136 is secured to support 118 by retainer 138 and to circular cylindrical preferably molded thermoplastic body 140 by retainer 142. Body 140 preferably is molded thermoplastic and comprises a circular cylinder. Body 140 has a projection 146 at its upper end for receiving an end of spring 136 and spring retainer 142. The opposite lower end of body 140 has a circular cylindrical projection 148 forming an annular shoulder 150. Art annular pliable rubber gasket 152 abuts the shoulder 150 and surrounds the projection 148.

The body 140 has an axially extending through core 144 in communication with the ambient atmosphere at both ends. The core 144 has a reduced diameter portion at the body upper end and through the projection 146 for closely receiving the shaft 130. An O-ring 147 may be included to provide a fluid tight seal between the shaft 130 and the body 140.

The shaft 130 has a portion in the axially extending core 144 and has a lower threaded end 154. The shaft 130 has an outer diameter smaller than the larger diameter of the core 144 to provide a clearance therebetween.

A preferably thermoplastic circular cylindrical plunger 158, e.g., teflon, has the same outer diameter as shaft 130 and a hollow core 160 of the same diameter as the shaft core 132 to form a continuous conduit therewith. The upper end of the plunger 158 has a metal coupler 159 secured thereto threaded to the threaded end 154 of shaft 130. In FIG. 3a, the plunger hollow core 160 is in communication with the plunger lower end 162. End 162 is rounded to somewhat the same shape as the bottom surface in interior of the cuvettes 116 as seen in FIG. 3, but of smaller radius.

In FIG. 3a, four radially extending conduits 164 at right angles to each other (two being shown in the figure) are in communication with the core 160 and the outer peripheral surface of the plunger 158 adjacent to end 162. The plunger 158 has an outer diameter of about the same as the shaft 130 and continues the clearance between the plunger 158 and the body 140 core 144. This clearance thus extends for the full length of the shaft 130 and the plunger in core 144 and forms a continuous fluid conduit. The plunger 158 outer diameter is dimensioned to provide a similarly dimensioned clearance to the inner surfaces of a cuvette 116 when the plunger is inserted in the cuvette to continue the clearance conduit formed with shaft 130.

Two conduits 166 and 168 are in body 140 in communication with core 144 and the body external region. Conduit 166 is connected to air supply tube 80 and conduit 168 is connected to diluent supply tube 82.

In operation of the wash assembly 84, at a time after the completion of a test cycle when the reacted fluids including blood serum and reagents, for example, have been tested, the cuvette with these fluids is rotated by the control 9. This occurs in a fluid handling cycle, e.g., 14 seconds, while the needle 35 is transferring test fluids to a cuvette. The cuvette is moved to a position where that cuvette is aligned with the plunger 158 on axis 126, FIG. 3. At this time, fluids are being applied to another cuvette as described below.

The control 9 operates the stepping motor rotating screw 124 which lowers the support 118 axially in direction 120'. This displaces the shaft 130 in direction 120'. The spring 136 is relatively stiff and displaces with the support 118. The spring 136 displaces the body 140 simultaneously with the support 118 and shaft 130.

When the gasket 152 engages the upper rim of the cuvette 116, an airtight seal therebetween is formed. Further displacement of the support 118 in direction 120' compresses the spring 136 further displacing the shaft 130 in direction 120'. This displaces the plunger 158 until it is closely spaced from the bottom of the cuvette as controlled by the stepping motor via control 9.

As a result of the sealing action of the gasket 152, the clearances between the plunger 158 with the body 140 and with the cuvette and between the shaft 130 with the body 140 form a continuous sealed ring shaped conduit between the plunger end 162 at the base of the cuvette 116 and tubes 80 and 82. The coupling of the plunger 158 to the shaft 130 and to tube 92 forms their hollow cores into a second sealed conduit. This latter conduit always has a vacuum applied via the connection to the vacuum source pump 100 manifold 96 (FIG. 1).

As the plunger end 162 becomes immersed in the fluids in the cuvette whose test is completed, the pinch valve 78 permits diluent to be drawn through the tube 82 and into the clearance in the body 140 core 144 in response to the vacuum applied by tube 92. The washing diluent flows into the cuvette while the vacuum immediately aspirates the test residual fluid which flows to the waste collector 90 (FIG. 1).

When the plunger reaches the position of FIG. 3, the waste fluid is completely aspirated while diluent flows into the cuvette, washing it. The body 140 is then lifted in the opposite direction 120' out of the cuvette. The diluent still flows into the cuvette and is continually aspirated at the same time. Also, the radial conduits 164 in the plunger displace axially adjacent to and clean the inner sides of the cuvette cavity as the plunger is lifted. This procedure is preferably repeated several times in different wash cycle portions, e.g., four times at a single wash station location.

In the last wash cycle portion, the pinch valve is operated by the control 9 closing the diluent flow to the tube 82 and opening the tube 80 to ambient air. The vacuum in the tube 92 applied to the end 162 openings 164 and core 160 of the plunger draws air from tubes 80 and 77 through the pinch valve 78. The air is drawn along the inner side of the cuvette and outer side of the plunger 158 to the end 162 drying the cuvette interior as the plunger is inserted and withdrawn from the cuvette. All four reciprocating actions of the plunger occur in the time period of the test fluids transfer to another cuvette, e.g., about 14 seconds.

The control 9 at the beginning of the next wash cycle opens the valve 78 diluent conduit 74' closing the air conduit 77' for cleaning the next cuvette which is now positioned at the wash station during the following fluid transfer cycle to transfer test fluids to a further cuvette. Thus during each transfer of fluids to one cuvette, a second cuvette is being automatically cleaned without adding time to the fluid transfer and test cycle.

Figure 4:
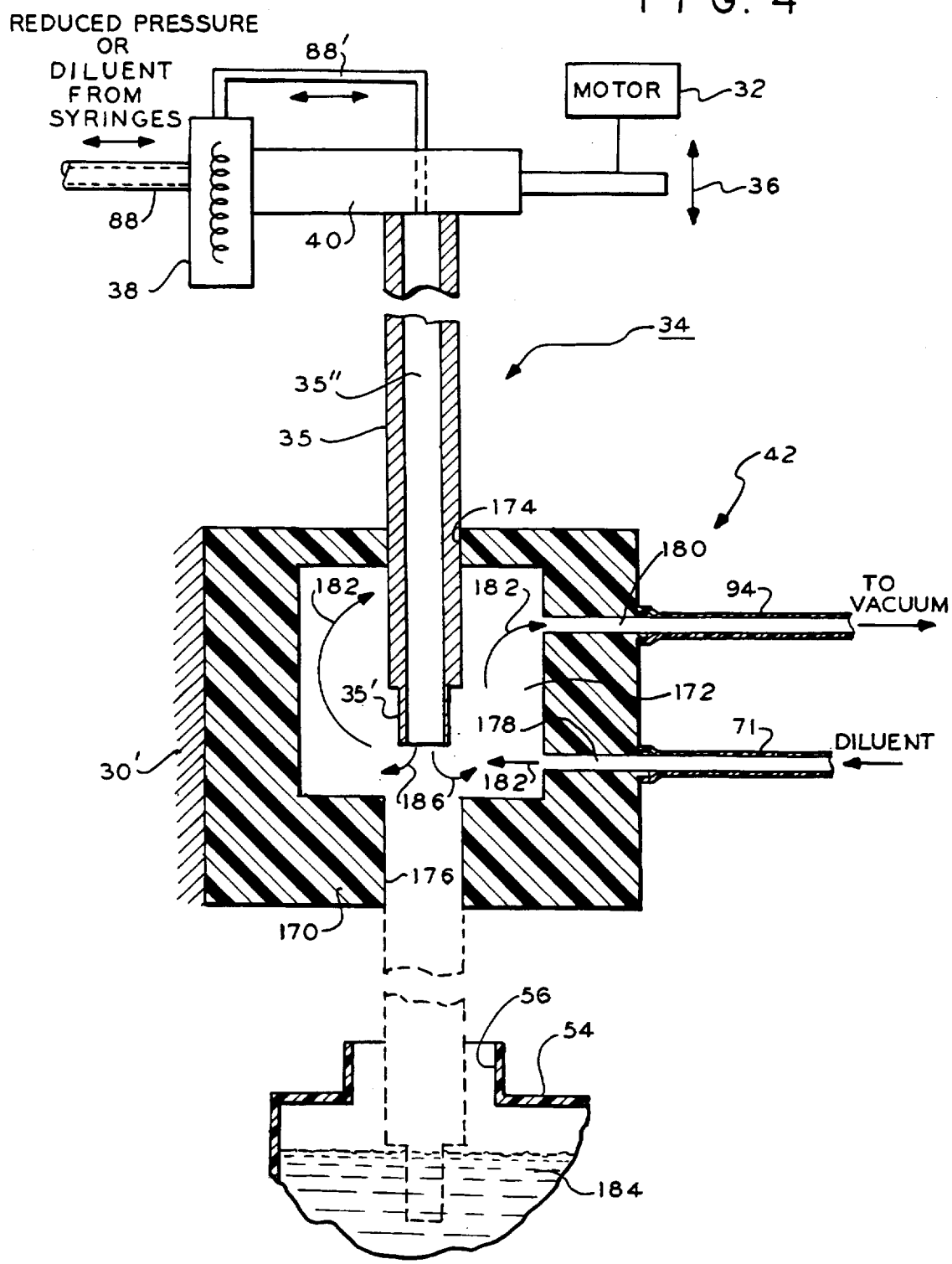
FIG. 4 is a partially diagrammatic fragmented sectional side elevation view of a needle washing device used in the embodiment of FIG. 1.

In FIG. 4, needle wash assembly 42 includes a preferably molded thermoplastic housing 170 secured fixed to arm 26 housing 30 represented by symbols 30'. The housing 170 has a circular cylindrical cavity 172. The housing 170 also has aligned through bores 174 and 176 in communication with the cavity 172. The bores 174 and 176 receive the needle 35 therethrough. The needle 35 reciprocates within the cavity 172 and bores 174 and 176 in directions 36. The needle 35 has a reduced diameter tip 35'.

Tube 71 is coupled to cavity 172 by conduit 178 and tube 94 is coupled to cavity 172 by conduit 180. The vacuum is always applied to cavity 172 via tube 94. The needle 35 core 35" is coupled to tube 88 through support 40, tube 88' and heater 38 for maintaining the temperature of the diluent supplied to the needle 35 as known. Tube 88 receives diluent from a selected one of the syringes 86 determined by control 9.

In operation of the wash assembly 42, the needle 35 is transferred to the reagent carousel from the home position at member 44, FIG. 2. The needle may be transferred to either of the openings 46 or 48 in the platform of the base 24, FIG. 1. The needle tip 35' is in the position shown in FIG. 4 during this transfer stage. When the control 9 generates an operating command signal to the arm 26 transfer stepping motor (not shown), a simultaneous command is generated and applied to the pump 70 motor (not shown). This causes the pump 70 to pump diluent to the tube 71.

The diluent is applied to cavity 172, FIG. 3, where the diluent flows in the directions 182 throughout the cavity 172 from conduit 178 to conduit 180 during the arm 26 transfer. The vacuum at conduit 180 draws the diluent in the directions 182. The diluent thus flows around the needle tip 35' washing it continuously during the arm transfer. The core 35" of the needle 35 does not draw in the diluent because no relative negative pressure is in the core 35".

In the next step of a test cycle, the pump 70 is shut off as the arm 26 is now stationary at its destination at one of openings 46 and 48. The needle 35 is lowered by motor 32 and support 40. This immerses the tip 35' into a reagent 184 a predetermined depth in a container 54 (shown in phantom). One of the syringes 86 (FIG. 1) is operated by a stepping motor in response to control 9 for creating a negative pressure in core 35" via tube 88. This draws a measured amount of reagent 184 into the needle core. This action also contaminates the needle tip 35' external surface with reagent.

The needle 35 is then lifted to the position shown in solid line in FIG. 4 at which time the arm 26 is again rotated to transport the needle 35 to the sample carrier 102, FIG. 2. The control 9 in the interim has aligned a sample container 106' for supplying sample, e.g., blood serum, to the needle 35. While the arm 26 and needle 35' are being transferred, the pump 70 is turned on simultaneously therewith, and the above described wash cycle for the tip 35' external surface is repeated.

When the arm and needle arrive at and aligned with a sample container 106', the pump 70 is turned off. The needle is lowered for immersion into the serum sample contained in the container 106'. One of syringes 86 then draws a measured amount of sample into the needle. This sample is spaced from the carried reagent by an air bubble in the needle core 35" created by the syringe. Air bubble separation is effected by drawing a first liquid into the needle 35, followed by drawing air into the needle and then drawing a further liquid into the needle. These steps are controlled by control 9. After this, the needle is lifted from the sample which also contaminates the tip 35' exterior surface.

Each time the arm is transported, the tip 35' is always in the position shown in FIG. 4. The needle with the sample and reagent are then transported over to the cuvette assembly 102 aligned with one of the cuvettes by control 9. The external surface of the needle tip is once again washed during this transfer as described above. One of the syringes then discharges the reagent and serum sample into that cuvette for test at which time the arm 26 is returned either to its home position or to the reagent carousel for a next test as desired. During this time the tip is once again washed as described.

However, during this transport cycle of the arm after the fluids are deposited into a cuvette, the needle core 35" is flushed with diluent by a syringe 86 while the tip 35' is in cavity 172, arrows 186. This liquid is drawn into tube 94 as described above and the liquids fed to the waste collector 90 as are all waste liquids drawn by vacuum into the different tubes. When the needle 35 is placed in the home position both its external surface and internal core are thus clean ready for the next test.

The cuvette wash cycle portions may be programmed for as many repetitive cycles as desired for a given implementation. Considerably less water or diluent is used in the wash cycles as in prior art systems, e.g., 1 liter per hour as compared to gallons in the prior systems.

Figure 5:
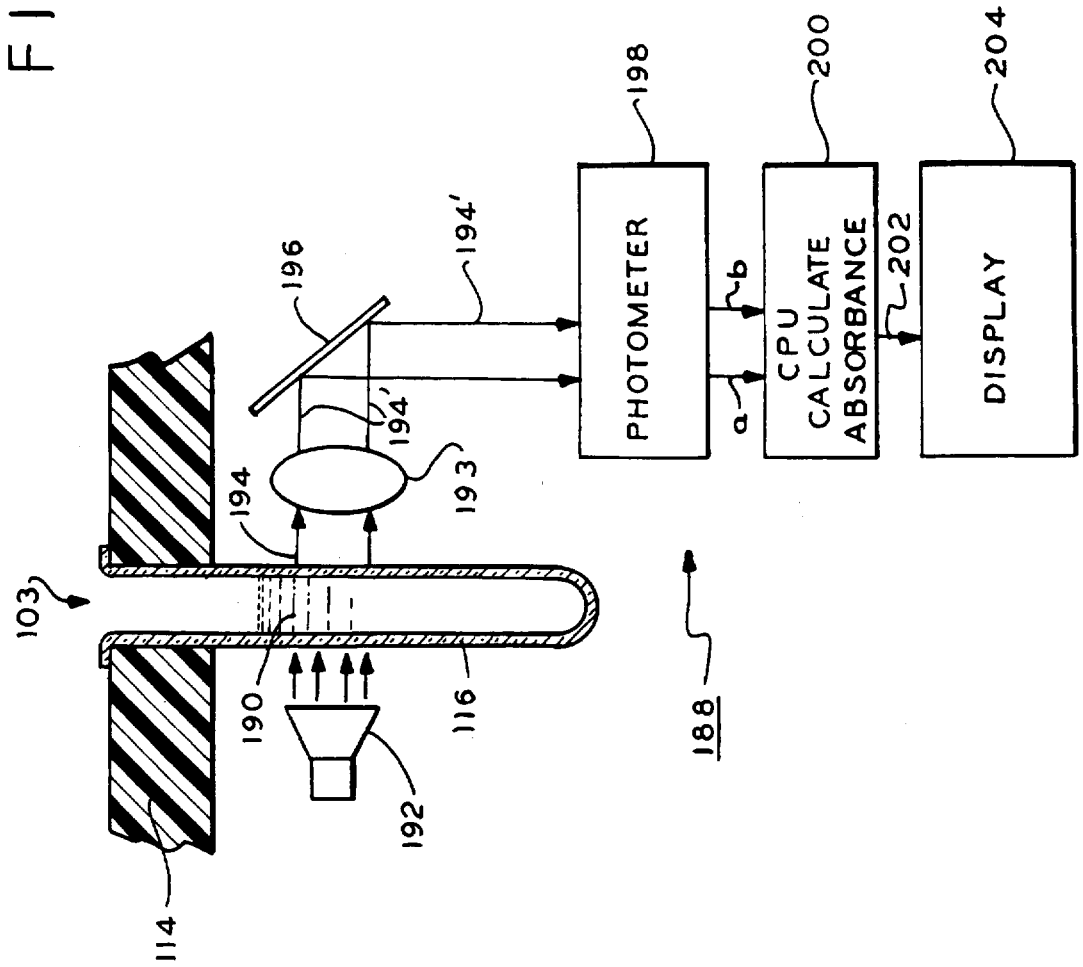
FIG. 5 is a partially diagrammatic side elevation sectional view of a colorimetric photometer arrangement used in the embodiment of FIG. 1.

In FIG. 5., a colorimetry photometer system 188 is illustrated for performing a colorimetric analysis of various samples such as blood serum and the like. In FIG. 5, system 188 is used to measure absorbance of light by a fluid 190 under test in a cuvette 116. A polychromatic light source 192, e.g., a halogen bulb, is located at a test location 103 (see also FIG. 2) adjacent to the cuvette assembly 102. The light rays are passed completely through the optically transparent cuvette 116 through the sample fluid 190 under test to a condensing lens 193.

A portion of the light incident on lens 193 is absorbed by the fluid 190. The measurement of the light 194 passed through the fluid in absorbance units is a measure of one or more components in the fluid. This is a wellknown test in this art and is employed in prior systems. See for example U.S. Pat. No. 4,942,017 mentioned in the introductory portion. The resulting light 194' from lens 192 incident on mirror 196 is reflected onto photometer 198. Photometer 198 produces two signals a and b simultaneously. Signal a represents the maximum peak output value of the light at one wavelength in millivolts and signal b represents a minimum value signal at a second different wavelength manifesting a baseline noise level.

A computer CPU 200, for example the 486 microprocessor in control 9, FIG. 1, receives those signals and calculates absorbance units for those signals. The output of the computer on line 202, which represents a multiple wire conductor cable, is applied to display 204 such as display 20, FIG. 2 or a printer (not shown) or both.

Figure 6:
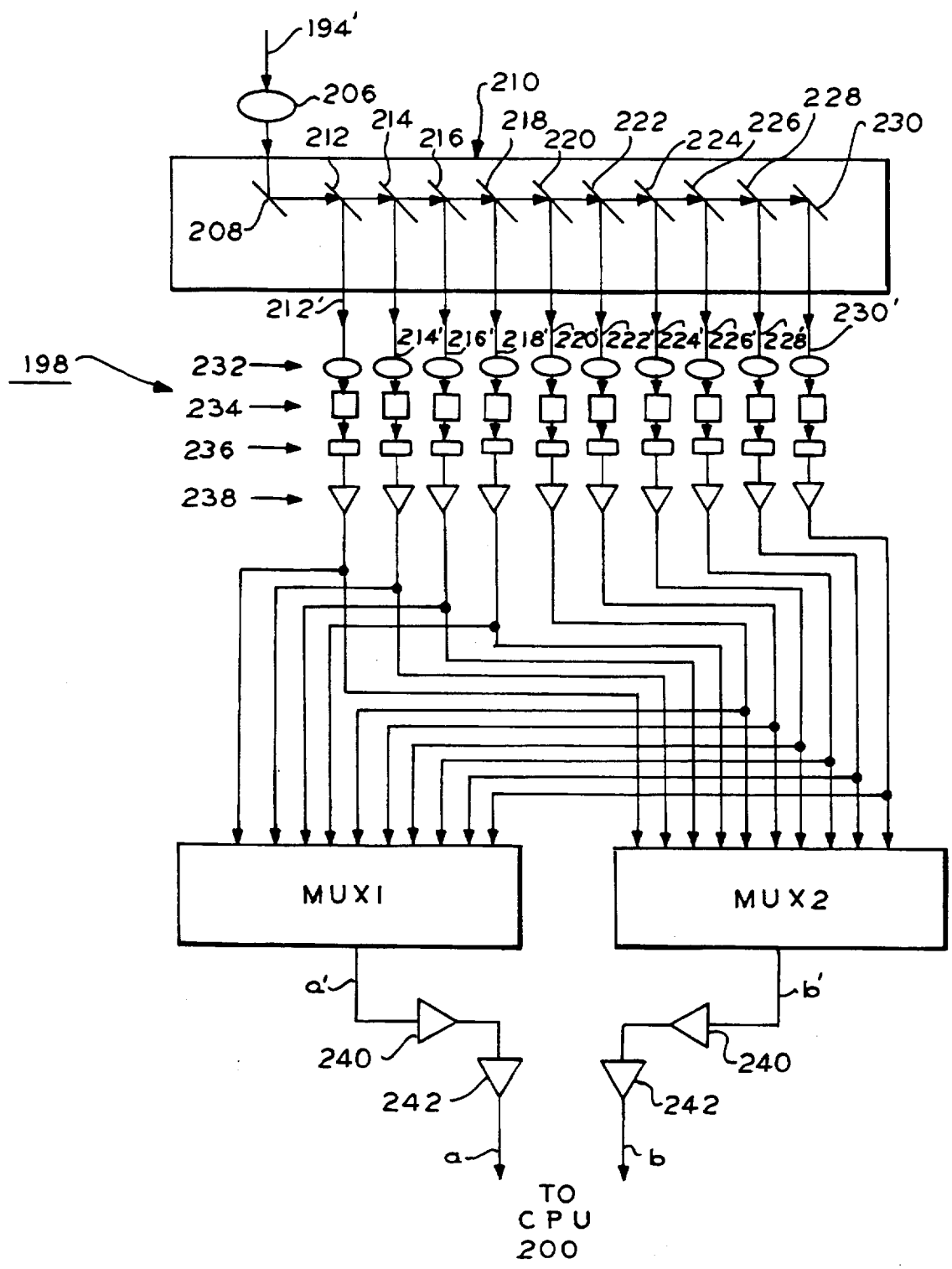
FIG. 6 is a circuit diagram of the photometer of FIG. 5.

The photometer 198, FIG. 6, includes a condenser lens 206 which focusses the light 194' onto a mirror 208 in mirror assembly 210. Assembly 210 is an array of ten mirrors 212–230 aligned with mirror 208. Mirrors 208 and 230 fully reflect all incident light rays. The remaining mirrors 212–228 partially reflect and partially transmit incident light. The assembly 210 is available as a package for mounting on a printed circuit board (not shown).

The corresponding reflected beams 212"–230" each containing substantially the same spectrum of light are each applied to a respective corresponding condenser lens of lens array 232. The output beam from each lens of array 232 is applied to a corresponding different narrow bandwidth interference filter in filter array 234. The filters have wavelengths from 340 nanometers (nm) (ultraviolet) to 700 nm (infrared). The particular wavelengths of each filter are known in this art and are used in prior art photometers mentioned in the introductory portion. For example, the filters may be respectively responsive to wavelengths of 340, 380, 405, 450, 492, 510, 546, 578, 630 and 700 nm. The output of each filter of array 234 is applied to a corresponding photodiode in photodiode array 236.

Each diode of array 236 is in circuit with a corresponding amplifier in amplifier array 238 for amplifying the diode output signals. The amplifiers of array 238 preferably include an operational amplifier with a parallel resistor-capacitor feedback network coupled to the inverting input of the amplifier and to a reference potential through the cathodeanode of the photodiode. The non-inverting inputs of the operational amplifiers are coupled to the reference potential. Unlike prior art photodiode circuits there is no gain adjustment in circuit with each such amplifier.

The output of each amplifier, which may be type AD 648, of array 238 is applied to two identical multiplexers mux 1 and mux 2, such as a 40678 integrated circuit. The outputs of the two multiplexers are two signals, signal a' produced by mux 1 and signal b' produced by mux 2. These output signals allow any two selected wavelengths, one from each multiplexer, to be read simultaneously.

These signals are amplified by further serially connected operational amplifiers 240 and 242, which may be type LM 350. The signals a' and b' are applied to the non-inverting inputs. The inverting inputs of amplifiers 240 have a feedback divider resistance coupled to a reference potential. The inverting inputs of amplifiers 242 have a direct feedback coupled to the non-inverting input through a parallel capacitor network.

The outputs of amplifiers 242 are each applied to an integrated prelogarithmic amplifier circuit of type PAL 110 (not shown) to collect data. These latter signals a and b are transmitted to the computer CPU 200 for logarithmic calculation of the absorbance units for each component in the fluid under test. This calculation subtracts the value of signal b from the value of signal a prior to performing the calculation of absorbance units. The photometric accuracy is +/– 1% from 0 to 2.5 Optical Densities.

Figure 8:
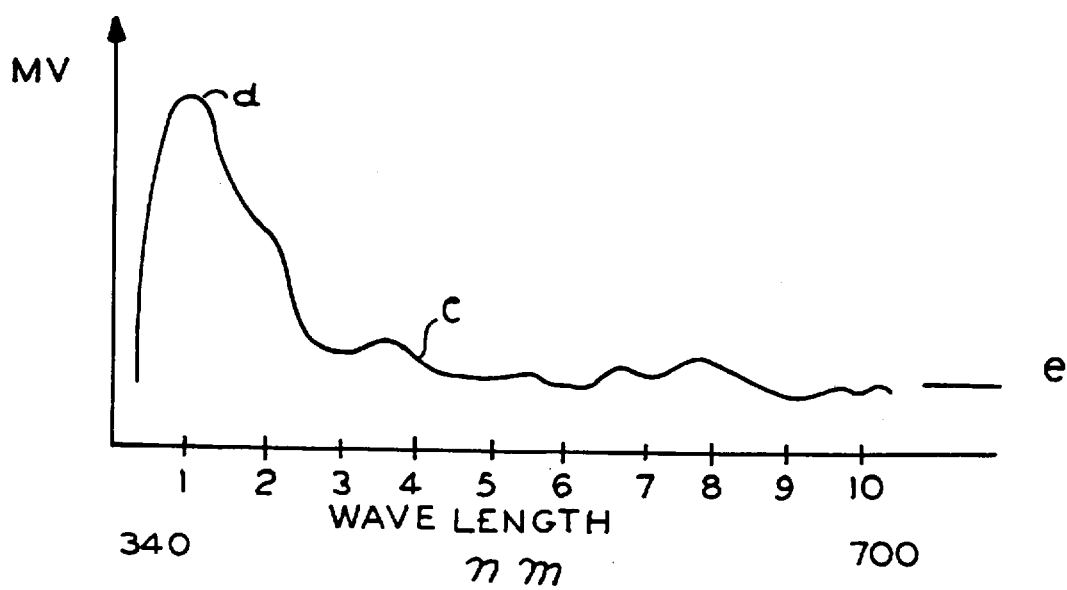

In FIG. 8, a chart is illustrated of a waveform generated by one component of the fluid under test, e.g., glucose. This chart represents a fingerprint for that component produced by the ten filters. A similar fingerprint is taken for all components of interest. The component represented by FIG. 8 produces a combined detected signal curve c from all of the filters of array 234. Curve c has a peak value d and a noise level e.

In blood serum, all components have a peak value at a given wavelength. Assume that the peak value d, at 340 nm, manifests, for example, the amount of glucose in the serum under test. Chlorestoral peaks at about 558 nm. These values are biased by noise manifested by base level, such as level e. Consequently, the value of level e is subtracted from the peak value d prior to performing the absorbance conversion.

This is accomplished by the CPU 200 programmed to preselect a signal from mux 2 representing a known noise wavelength and a signal from mux 1 representing a known peak value at a given wavelength which are simultaneously generated from the sample under test. This produces a bichromatic reading as compared to monochromatic readings in prior systems. The control 9 is preprogrammed to know which signals to expect as peak and which are noise for the full range of different components sensed by the detector photodiodes of array 234 and of interest for producing a calculated result.

This calculation is logarithmic and is the logarithm of the difference between the amount of light that possibly can be detected (baseline value) and the amount of light that is absorbed (the unknown). This difference is converted to absorbance units manifesting the amount of the component detected. This is a more accurate and reliable reading than the prior art system employing adjustable potentiometers for setting the output values for each discrete component of interest corresponding directly to absorbance values. Further, those prior art values are artificially limited by setting the maximum and minimum values of the detected output signal, curve c, with the adjustments.

Figure 7:
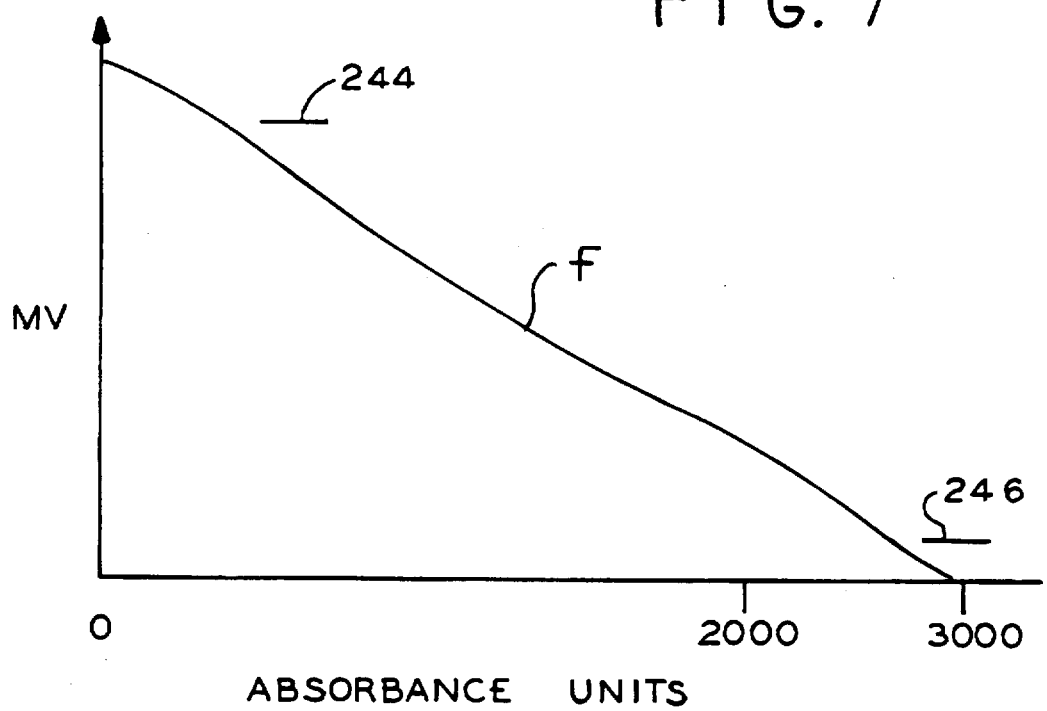
FIGS. 7 and 8 are charts useful for explaining some of the principles of the photometer of FIGS. 5 and 6.

In FIG. 7, the full range of possible output signals from all of the filters is given by curve f. This range of values is artificially limited at levels 244 and 246 as explained in the introductory portion. As a result prior systems whose measurements exceed these preset limits needed to be retested by diluting the sample.

This repetitive dilution step occurs minimumly in the present photometer which utilizes the full range of output signals produced by the filters. The calculation is under control of the microprocessors in control 9. All of the circuit and components of FIG. 6 may be on a single printed circuit board. All of the calculations are performed in sequence on all cuvettes, e.g., 25 cuvettes in 14 second test cycles, for example. The present system thus has an increased scale range and greater versatility than prior systems precluding unnecessary reruns of a sample under test. The photometer is calibrated with a clear diluent in a cuvette and the reading calibrated to zero.

The system 2 can perform 500 automated tests per hour or about 7 seconds per test. This is a significant increase in capacity as compared to prior systems having a throughput of about 75 tests per hour.

The wash cycles for the cuvette can be programmed to increase or decrease the number of repetitions for a given implementation. The cuvette wash assembly may use about 1 liter per hour in a fully automatic mode.

In operation, the analyzer 2 operating computer program is loaded into the control 9 via floppy drive 16 at the factory. This program is used throughout the life of the analyzer 2 unless updated periodically as desired. The microprocessors of the control 9 direct the control activities in conjunction with the Z80 microprocessors (not shown). The tests are conducted by an operator using the computer 18, keyboard 22 via appropriate menus displayed on display 20 and a mouse (not shown) for selecting the test parameters and for starting the test procedure.

The desired reagents are placed in containers 54 in the appropriate predesignated order which is preprogrammed into control 9. The protocol for the tests are set up by the operator at the keyboard 22. The desired fluid samples under test such as blood serum are placed in the various containers 106 also in the predetermined order as preprogrammed in the control 9. The protocol for these reagents are entered into the system by the operator via keyboard 22. All of the cuvettes 116 are empty and clean with one of the cuvettes in position for receiving fluids via arm 26 and needle 35.

The test sequence is commenced and arm 26 is then automatically moved first to one or more reagents according to a particular test being conducted. During this movement of the needle to the reagent carousel 52, the needle 35 is automatically being cleaned as described above. Also, the control 9 rotates the reagent carousel 52 and places the appropriate reagent container 54 in position for access by the needle 35 as determined by the test protocol.

The needle 35 tip 35' is then immersed in the reagent which immersion is sensed by a sensor (not shown) for automatically detecting and measuring the volume of reagent in the container 54 in a known manner to make certain sufficient reagent is present. The immersed needle then withdraws the desired amount of reagent under control of a syringe 86 operated by control 9. If a second reagent is needed, bubble separation is effected, and is also withdrawn into the needle 35. However, the needle tip external region is automatically washed by the assembly 42 before picking up the second reagent.

The arm 26 is then transferred to the carrier 2 to a preselected container 106 placed in the preprogrammed position by the stepping motor operating the turntable 104 as determined by control 9. During the transfer, the needle external surface at the tip 35' is washed and reagents removed that may cling to the needle external surface. The washing cycle of the needle stops when the arm and needle reach their destination. The needle is immersed in a sample to be tested and the sample withdrawn into the needle separated from the reagents by an air bubble. The arm 26 is then transferred to a preselected reaction cuvette 116 at assembly 112 and the needle washed externally again during transfer. The needle contents are discharged via a syringe 86 under control of control 9.

The arm then returns to either to the home position or to the reagent carousel. In the interim, during arm transfer, the needle tip exterior is once again cleaned. Also, at this time the needle core is flushed by a diluent discharged therethrough by a syringe 86. All contaminants during each wash step are withdrawn by the vacuum and deposited into the waste collector 90. The cycle is then repeated for each fluid transfer. Each fluid handling cycle occurs within a 14 second period.

The arm 26 commences a new cycle of collecting fluids for the next test by depositing the test fluids in a corresponding preselected cuvette. Cuvette assembly 112 is rotated to place the next preselected cuvette in position to receive the test fluids including the sample and reagent or reagents for the next test. During each fluid handling cycle, one of the cuvettes is cleaned at the wash station by washer assembly 84.

At the end of each fluid handling cycle, the 25 cuvettes, some of which contain test fluids therein and some of which may be empty, are rotated to the photometric test system 188. The photometric tests on the fluids in the cuvettes is commenced after the appropriate reaction times have elapsed as determined by control 9. The photometric system 188 reads the light 194 transmitted through each cuvette 116 as the cuvettes move past the light source 192, FIG. 5. This photometric reading cycle preferably occurs within 2 seconds in which all 25 cuvettes are rotated past the photometric system 188 for reading the preselected tests.

Not all cuvettes have a photometric test performed in each 2 second photometric reading cycle. This 2 second cycle occurs after each fluid handling cycle. The information of the photometric test for all of the cuvettes exhibiting readings in that cycle is collected and stored in memory and ultimately displayed on display 20 and/or printed by a printer. The results may be communicated via modem and the like to a remote receiving station as described in the aforementioned U.S. Pat. No. 5,271,899.

Thus, the photometric tests on the fluids in the cuvettes occurs intermediate the readying of a next cuvette for receiving its test fluids. Therefore each full rotation of the cuvette turntable results in a photometric test after the designated reaction time for each cuvette. During a fluid handling cycle as the fluids are being transferred to one cuvette, a second cuvette is being washed by assembly 84. Since the cuvettes are each cleaned at one cleaning station, the washing cycle is shorter than in prior systems and can be conducted within the time allotted to transfer all of the required fluids to a cuvette.

The analyzer disclosed herein is of the random type in which the tests conducted in each cuvette may be randomly related. That is, different photometric tests may be completed on successive cuvettes regardless the sequence of the tests.

The above system including work station section 6 is under control of programmable control section 4. Control section 4 is linked to the computer 18 by a bidirectional communications interface. This interface is used to communicate patient requirements to the control section 4 and to receive the associated test results from the control section 4. All control functions can be randomly initiated under control of scheduling software provided the computer 18 to match pending requisition requirements and current instrument status conditions.

It will occur to one of ordinary skill that various modifications may be made to the disclosed system without departing from the scope of the invention as defined in the appended claims.

What is claimed is:

1. A chemical analyzer system comprising:

cuvette means including a plurality of cuvettes;

sample holding means for holding a plurality of samples;

reagent holding means for holding at least one reagent;

transfer means including a needle having an external surface and a hollow core insertable into and for receiving at least a portion of one of said samples and at least a portion of said at least one reagent and for transferring the received portions to one of said cuvettes, said transferring of each portion occurring in a period of a given duration, said received portions forming a test sample in said one cuvette;

needle washing means including means for washing the needle external surface continuously during substantially the entire duration of said transferring periods of said portions and for washing the needle core subsequent to said transferring periods of said portions;

cuvette cleaning means comprising plunger means including a single plunger for reciprocating within said one cuvette subsequent to said transferring for automatically washing, aspirating and drying the one cuvette during said reciprocating at one cleaning location;

colorimetric photometer means including light generating means and a plurality of filter means responsive to the light from the light generating means passed through the test sample for producing a plurality of signals each corresponding to a different filter means and manifesting a different wavelength of said passed through light; and calculating means responsive to said signals for generating an output signal manifesting a calculated light absorbance value of said test sample.

2. The system of claim 1 wherein said transfer means includes means for transferring the needle to and from a home station, said needle washing means including means for washing the needle external surface while the needle is in motion between said home station and each said cuvette means, sample holding means and reagent holding means.

3. The system of claim 1 including a diluent fluid and vacuum means for creating a vacuum, means for coupling the fluid and the vacuum to said plunger means and to said needle washing means for drawing said fluid into and out of said one cuvette and for drawing said fluid about said needle surface in response to said vacuum to effect said washing of said cuvette and needle surface.

4. The system of claim 3 including pump means for applying said fluid under pressure to said needle washing means.

5. The system of claim 3 including syringe means for applying fluid to said needle core for diluting said received reagent and sample during said transferring and for washing said core.

6. The system of claim 1 wherein said plunger means is for cleaning one cuvette at a time at one station location, each said cuvettes having a cylindrical cavity, the plunger comprising a cylindrical member having an outer peripheral surface and an end for insertion into said cavity of an associated cuvette, said inserted plunger and associated cuvette defining a region therebetween, said plunger having an axial bore in communication with said end of the plunger and a plurality of radial bores in communication with the axial bore and the outer peripheral surface of the plunger and means for applying a vacuum to said axial bore and for alternately applying wash fluid and air to the region between the plunger and the cuvette to effect alternating washing and drying of said one cuvette in respective aspirating, washing and drying reciprocating cycles at said one station location wherein each cycle corresponds to a selected one of said aspirating, washing and drying in response to said vacuum withdrawing said applied fluid and air in said region.

7. The system of claim 6 wherein the outer peripheral surface of the inserted plunger member defines a clearance space with the cuvette cavity for receiving said fluid and air, said means for applying said wash fluid and air including means for cyclically effecting said washing and drying of said one cuvette.

8. The system of claim 1 wherein said plunger means comprises a support, means for vertically reciprocating said support, means for securing the plunger to said support for reciprocating displacement therewith, said plunger having a hollow first core, a body having a hollow second core for movably receiving said plunger therein and resiliently secured to said support for vertical displacement with said support, a gasket secured to said body for sealing resilient engagement with said one cuvette in response to said reciprocating support and means for applying a negative pressure to said first core and for selectively fluid coupling one at a time air and a washing fluid to said second core.

9. The system of claim 8 wherein said second hollow core defines a fluid chamber surrounding said plunger, said chamber forming a continuous chamber with said one cuvette with said gasket engaged, and means for sealing said chamber between said body and said plunger distal said gasket so that the chamber remains fluid sealed while said plunger reciprocates within said chamber.

10. The system of claim 1 wherein said sample holding means comprises a plurality of tubes each for holding a different sample, said reagent holding means include a plurality of containers each for holding at least one reagent, each said cuvette means, sample holding means and reagent holding means comprising a rotatable carousel, and further including means for causing said transfer means to transfer a plurality of said samples and a plurality of said reagents to a plurality of said cuvettes in a sequence, said cuvette washing means includes means for washing, aspirating and drying each cuvette sequentially one at a time during said sequence.

11. The system of claim 1 wherein said filter means includes a plurality of filters each for generating a corresponding output signal manifesting a given component of said sample, first amplifier means for amplifying each said output signals, multiplexer means responsive to said output signals for generating at least one multiplexed signal and second amplifier means for amplifying said at least one multiplexed signal.

12. The system of claim 11 wherein said multiplexer means comprises first and second multiplexers each for receiving said output signals of each said plurality of filters, said at least one multiplexed signal comprising third and fourth simultaneously generated like multiplexer signals, said calculating means including means for subtracting the fourth signal from said third signal corresponding to each said filters to remove a noise component from said third signal and means for calculating said absorbance values.

13. A chemical analyzer system comprising:

cuvette means including a plurality of cuvettes;

sample holding means for holding a plurality of samples;

reagent holding means for holding at least one reagent;

transfer means including a needle having an external tip surface and a hollow core insertable into and for receiving at least a portion of one of said samples and at least a portion of said at least one reagent and for transferring the received portions to one of said cuvettes in a corresponding portion transfer cycle having a period of a given duration; and needle washing means including means for washing the needle external surface during substantially the entire period of each said transfer cycles and for washing the needle core after the completion of all said cycles.

14. The system of claim 13 wherein said transfer means includes means for transferring the needle to and from a home station, said needle washing means including means for washing the needle external surface while the needle is in motion between said home station and each said cuvette means, sample holding means and reagent holding means.

15. The system of claim 13 including a diluent fluid and vacuum means for creating a vacuum, means for coupling the fluid and the vacuum to said needle washing means for drawing said fluid into and out of said hollow core and for drawing said fluid about said needle surface in response to said vacuum applied to said hollow core and needle surface to effect said washing of said core and needle surface.

16. The system of claim 13 wherein said needle washing means comprises a housing having a single central cavity and aligned first and second through bores in fluid communication with the cavity and the ambient atmosphere for receiving the needle, means for reciprocating said needle in the bores and said cavity and for selectively locating said needle in said cavity, and further comprising means for selectively applying a diluent fluid to said needle core and a vacuum and washing fluid to said cavity.

17. The system of claim 15 including syringe means for applying fluid to said needle core for diluting said received reagent and sample and for washing said core.

18. A chemical analyzer system comprising:

cuvette means including a plurality of cuvettes each having a cuvette cavity;

sample holding means for holding a plurality of samples;

reagent holding means for holding at least one reagent;

transfer means for transferring at least a portion of one of said samples and at least a portion of said at least one reagent to one of said cuvettes;

test means for testing the one sample combined with the at least one reagent for at least one parameter in said one cuvette; and cuvette washing means including plunger means comprising sealing means for sealing said one cuvette cavity during washing of said one cuvette and a single plunger for reciprocating within said one cuvette cavity subsequent to said testing at one wash location of said one cuvette for automatically aspirating, washing and drying the one cuvette sealed cavity at the one cuvette location during said reciprocating in respective aspirating, washing and drying reciprocating cycles of the one cuvette at said one wash location wherein each cycle corresponds to a selected one of said aspirating, washing and drying.

19. The system of claim 18 wherein the plunger comprises a cylindrical member for insertion in said one cuvette cavity and defining a region in the cavity between the one cuvette and plunger, said plunger having an axial bore in communication with an end of the plunger and a plurality of radial bores in communication with the axial bore and the outer peripheral surface of the plunger and means for applying a vacuum to said axial bore and for alternately applying a wash fluid and air to the region between the plunger and the cuvette to effect said cyclically occurring washing, aspirating and drying of said one cuvette cavity.

20. The system of claim 19 wherein the outer peripheral surface of the inserted plunger member defines a clearance space in said region with the cuvette cavity for receiving said fluid and air.

21. The system of claim 18 wherein said sealing means includes gasket means for providing an airtight seal between said plunger means and said one cuvette.

22. In a chemical analyzer system comprising cuvette means including a cuvette, sample holding means for holding a sample and reagent holding means for holding at least one reagent, the combination comprising:

transfer means including a needle having an external tip surface and a hollow core for insertion into and for receiving at least a portion of one of said samples and at least a portion of said at least one reagent and for transferring the received portions to a cuvette of said cuvette means in a corresponding portion transfer cycle having a period of a given duration; and needle washing means including means for washing the needle external surface continuously during substantially the entire period of each said transferring cycles and for washing the needle core after the completion of all said cycles.

* * * * *